(12) United States Patent
Tokumoto et al.

(10) Patent No.: US 9,498,611 B2
(45) Date of Patent: Nov. 22, 2016

(54) APPLICATOR

(71) Applicant: HISAMITSU PHARMACEUTICAL CO., INC., Tosu-shi, Saga (JP)

(72) Inventors: Seiji Tokumoto, Tsukuba (JP); Makoto Ogura, Tsukuba (JP)

(73) Assignee: HISAMITSU PHARMACEUTICAL CO., INC., Tosu-shi, Saga (JP)

( * ) Notice: Subject to any disclaimer, the term of this patent is extended or adjusted under 35 U.S.C. 154(b) by 0 days.

(21) Appl. No.: 14/349,523

(22) PCT Filed: Oct. 2, 2012

(86) PCT No.: PCT/JP2012/075534
§ 371 (c)(1),
(2) Date: Apr. 3, 2014

(87) PCT Pub. No.: WO2013/051568
PCT Pub. Date: Apr. 11, 2013

(65) Prior Publication Data
US 2014/0243747 A1    Aug. 28, 2014

(30) Foreign Application Priority Data
Oct. 6, 2011  (JP) .............................. P2011-222236

(51) Int. Cl.
*A61M 37/00*   (2006.01)
*A61B 5/151*   (2006.01)
*A61B 5/15*    (2006.01)

(52) U.S. Cl.
CPC ....... *A61M 37/0015* (2013.01); *A61B 5/15117* (2013.01); *A61B 5/150984* (2013.01);
(Continued)

(58) Field of Classification Search
CPC ................. A61M 2037/0023; A61M 37/0015; A61M 2037/003–2037/0061; A61B 2017/925
See application file for complete search history.

(56) References Cited

U.S. PATENT DOCUMENTS 1,033,099 A   7/1912   Harrison
2,932,277 A   4/1960   Borah
(Continued)

FOREIGN PATENT DOCUMENTS

CN      3643922       5/2007
CN      100591386 C   2/2010
(Continued)

OTHER PUBLICATIONS

WO Patent Application No. PCT/JP2011/073129, Search Report dated Nov. 22, 2011 six (6) pages.
(Continued)

*Primary Examiner* — Laura Bouchelle
*Assistant Examiner* — Anh Bui
(74) *Attorney, Agent, or Firm* — Nath, Goldberg & Meyer; Joshua B. Goldberg; Tanya E. Harkins

(57) ABSTRACT

An active agent is effectively administered without giving fear to the user when the microneedles are applied. An applicator 10 includes a transmission member that transmits biasing force of a biasing member to a microneedle array including micro projections (microneedles) with a needle density of 500 needles/cm² or more. The transmission member has a mass of 1.5 g or less, and the transmission member activated by the biasing force of the biasing member has a momentum of from 0.0083 (N·s) to 0.015 (N·s).

3 Claims, 15 Drawing Sheets

(52) U.S. Cl.
CPC ............... *A61M 2037/0023* (2013.01); *A61M 2037/0046* (2013.01); *A61M 2037/0061* (2013.01)

(56) References Cited

U.S. PATENT DOCUMENTS

| | | | |
|---|---|---|---|
| 4,526,171 | A | 7/1985 | Schachar |
| 4,589,412 | A | 5/1986 | Kensey |
| 4,747,842 | A | 5/1988 | Dietz |
| 5,026,388 | A | 6/1991 | Ingalz |
| 5,904,664 | A | 5/1999 | Kim |
| 6,298,863 | B1 | 10/2001 | Byun |
| 6,743,211 | B1 | 6/2004 | Prausnitz et al. |
| 7,381,003 | B1 | 6/2008 | Chang |
| 7,419,481 | B2 | 9/2008 | Trautman et al. |
| D598,173 | S | 8/2009 | Hartel |
| D612,939 | S | 3/2010 | Boone, III et al. |
| 7,914,813 | B2 | 3/2011 | Adachi et al. |
| 7,993,871 | B2 | 8/2011 | Skiffington et al. |
| 2002/0077584 | A1* | 6/2002 | Lin et al. ............... 604/21 |
| 2002/0087182 | A1 | 7/2002 | Trautman et al. |
| 2002/0123675 | A1 | 9/2002 | Trautman et al. |
| 2004/0087893 | A1 | 5/2004 | Kwon |
| 2005/0096586 | A1 | 5/2005 | Trautman et al. |
| 2005/0261631 | A1 | 11/2005 | Clarke et al. |
| 2006/0142691 | A1* | 6/2006 | Trautman ............ A61B 5/1411 604/46 |
| 2007/0083151 | A1 | 4/2007 | Carter |
| 2007/0233011 | A1 | 10/2007 | Hagino et al. |
| 2007/0250018 | A1 | 10/2007 | Adachi et al. |
| 2007/0255251 | A1 | 11/2007 | Panchula et al. |
| 2007/0293816 | A1 | 12/2007 | Chan et al. |
| 2008/0009811 | A1 | 1/2008 | Cantor |
| 2008/0114298 | A1 | 5/2008 | Cantor et al. |
| 2008/0183144 | A1 | 7/2008 | Trautman et al. |
| 2009/0030365 | A1 | 1/2009 | Tokumoto et al. |
| 2009/0099502 | A1 | 4/2009 | Tokumoto et al. |
| 2009/0130127 | A1 | 5/2009 | Tokumoto et al. |
| 2009/0216215 | A1 | 8/2009 | Thalmann et al. |
| 2010/0030100 | A1 | 2/2010 | Tokumoto et al. |
| 2010/0047327 | A1 | 2/2010 | Kuwahara et al. |
| 2010/0221314 | A1 | 9/2010 | Matsudo et al. |
| 2010/0249651 | A1 | 9/2010 | Hagino |
| 2010/0280457 | A1 | 11/2010 | Tokumoto et al. |
| 2011/0112509 | A1 | 5/2011 | Nozaki et al. |
| 2011/0172639 | A1 | 7/2011 | Moga et al. |
| 2011/0276027 | A1 | 11/2011 | Trautman et al. |
| 2011/0276028 | A1 | 11/2011 | Singh et al. |
| 2011/0319920 | A1 | 12/2011 | Kikkawa et al. |
| 2012/0130306 | A1 | 5/2012 | Terahara et al. |
| 2012/0136312 | A1 | 5/2012 | Terahara et al. |
| 2012/0330250 | A1 | 12/2012 | Kuwahara et al. |
| 2013/0041330 | A1 | 2/2013 | Matsudo et al. |
| 2013/0226098 | A1 | 8/2013 | Tokumoto et al. |

FOREIGN PATENT DOCUMENTS

| | | |
|---|---|---|
| CN | 102076357 A | 5/2011 |
| JP | 2002-522170 A | 7/2002 |
| JP | 2004-510534 A | 4/2004 |
| JP | 2004-510535 A | 4/2004 |
| JP | 2005533625 A | 11/2005 |
| JP | 2006-341089 A | 12/2006 |
| JP | 2007-037626 A | 2/2007 |
| JP | 2007-509706 A | 4/2007 |
| JP | 2007516781 A | 6/2007 |
| JP | 2007-260351 A | 10/2007 |
| JP | 4198985 B2 | 10/2008 |
| JP | 2010-501211 A | 1/2010 |
| JP | 2010-233803 A | 10/2010 |
| JP | 2011-078711 A | 4/2011 |
| KR | 30-0289753 | 1/2002 |
| KR | 30-0451541 | 6/2007 |
| TW | 132699 | 12/2009 |
| TW | 133128 | 1/2010 |
| WO | 00/09184 A1 | 2/2000 |
| WO | 02/30300 A2 | 4/2002 |
| WO | 2005123173 A1 | 12/2005 |
| WO | 2011/105508 A1 | 9/2011 |
| WO | 2012/046816 A1 | 4/2012 |

OTHER PUBLICATIONS

Taiwanese Design Patent Application No. 100301892, Notice of Allowance issued Nov. 14, 2011, four (4) pages.
WO Patent Application No. PCT/JP20111073129, International Preliminary Report on Patentability issued on May 16, 2013, Seven (7) pages.
WO Patent Application No. PCT/JP2012/075534, International Preliminary Report on Patentability dated Apr. 17, 2014, seven (7) Pages.
PCT/JP2012/075534, International Search Report dated Nov. 20, 2012, one (1) page.
European Patent Application No. 13771861.5, Search Report dated Dec. 16, 2015, eleven (11) pages.
Chinese Patent Application No. 201380017762.6, Office Action dated Nov. 27, 2015, seven (7) pages.
Japanese Patent Application No. P2012-537766, Notice of Allowance dated Feb. 2, 2016, three (3) pages.
Taiwan Patent Application No. 101136676, Office Action dated Dec. 29, 2015, four (4) pages.
European Patent Application No. 12838997.0, Search Report dated Nov. 11, 2015, seven (7) pages.

* cited by examiner (a)

(b)

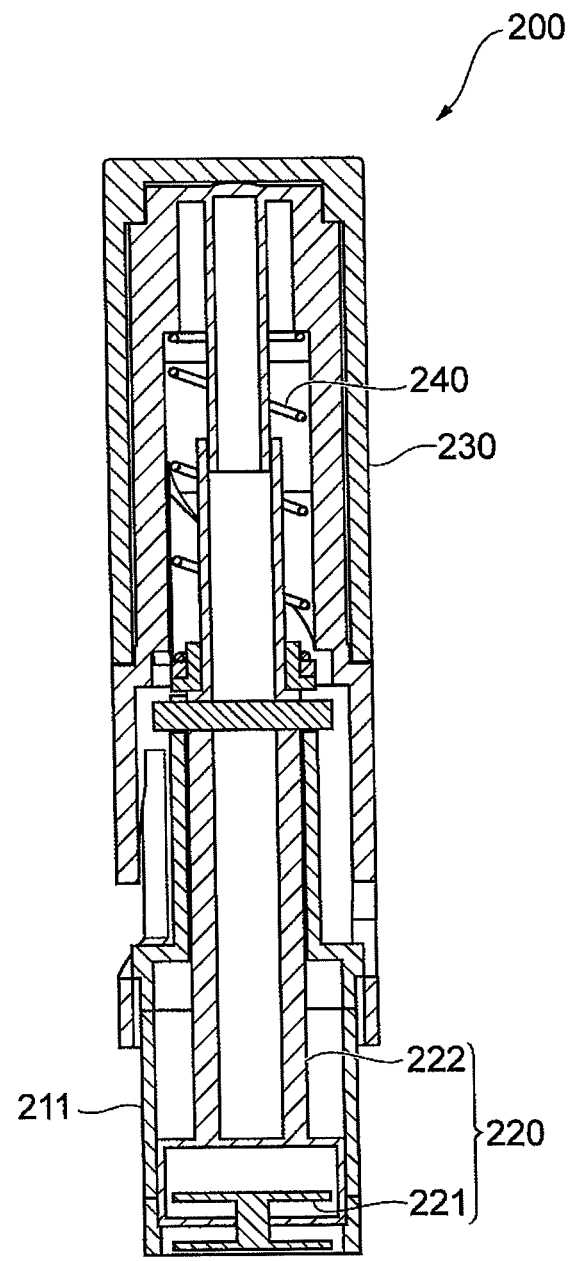

APPLICATOR

This is a National Phase Application filed under 35 U.S.C. §371 as a national stage of PCT/JP2012/075534, filed on Oct. 2, 2012, an application claiming the benefit under 35 U.S.C. §119 of Japanese Application No. P2011-222236, filed on Oct. 6, 2011, the content of each of which is hereby incorporated by reference in their entirety.

TECHNICAL FIELD

One embodiment of the present invention relates to an applicator used for assisting administration of an active agent with microneedles.

BACKGROUND ART

There has been conventionally known an applicator that makes an impact on a microneedle array administering an active agent through a skin so as to apply microneedles included in the microneedle array to the skin.

For example, the following Patent Literature 1 discloses an applicator that includes a device body, a piston for impacting a penetrating member with a stratum corneum, an impact spring for providing an impact force to the piston, a hold down spring operating between the device body and a cap, and a lock mechanism for compressing the device body and the piston together with compressing force so as to cock and lock the piston in a cocked position.

The following Patent Literature 2 discloses an applicator that includes a housing, a piston movable within the housing, and a cap.

The following Patent Literature 3 discloses an insertion device for applying an insertion head that includes an infusion cannula or a puncturing tip introduced into a body of a patient. The device includes two actuation members, which have to be actuated simultaneously to trigger the insertion movement.

The following Patent Literature 4 discloses a puncture device including a drive spring in which one end of the drive spring is not fixed to a housing side contact section or a piston.

PATENT LITERATURE

Patent Literature 1: Japanese Patent No. 4198985
Patent Literature 2: Publication of Japanese Translation of PCT Application No. 2007-509706
Patent Literature 3: Publication of Japanese Translation of PCT Application No. 2010-501211
Patent Literature 4: Japanese Patent Application Laid-Open Publication No. 2010-233803

SUMMARY OF INVENTION

Technical Problem

Using the above-mentioned applicators, a user can effectively administer an active agent; however, such applicators make an impact of a prescribed level or more on a skin. This may cause the user to fear of application of microneedles using the applicators. Thus, it is requested that an active agent be effectively administered to the user without fear when applying the microneedles.

Solution to Problem

An applicator in accordance with one embodiment of the present invention is the one for applying microneedles to a skin, and includes a transmission member that transmits biasing force of a biasing member to a microneedle array including microneedles with a needle density of 500 needles/cm$^2$ or more. A mass of the transmission member is 1.5 g or less, and a momentum of the transmission member activated by the biasing force of the biasing member is from 0.0083 (N·s) to 0.015 (N·s).

In this embodiment, the transmission member transmitting the biasing force necessary for puncture to the microneedle array is very light, and the user feels less impact during operation of the applicator. The user, therefore, can administer the active agent using the applicator without fear. In addition, even if the transmission member is lightened in order not to give fear to the users, the active agent can be effectively administered by setting the momentum of the transmission member and the needle density of the microneedles as described above.

In the applicator in accordance with another embodiment, a transfer amount of the active agent applied on the microneedles to a skin may be proportional to the momentum of the transmission member.

In the applicator in accordance with still another embodiment, the biasing member may be an elastic member, and the transmission member may move without receiving the biasing force of the elastic member in a first section forming a part of a movement section in which the transmission member moves toward the skin.

The applicator in accordance with still another embodiment may further include a support base that supports the elastic member and transmits the biasing force to the transmission member in a second section different form the first section. The support base pushed the transmission member with the biasing force stops at one end of the second section, the transmission member may move without receiving the biasing force in the first section.

The biasing member of the applicator in accordance with still another embodiment may be a column coil spring.

Advantageous Effects of Invention

According to one aspect of the present invention, an active agent can be effectively administered to a user without fear when applying microneedles.

BRIEF DESCRIPTION OF DRAWINGS

FIG. 15 is a sectional view along line XV-XV of FIG. 14.

DESCRIPTION OF EMBODIMENTS

Figure 1:
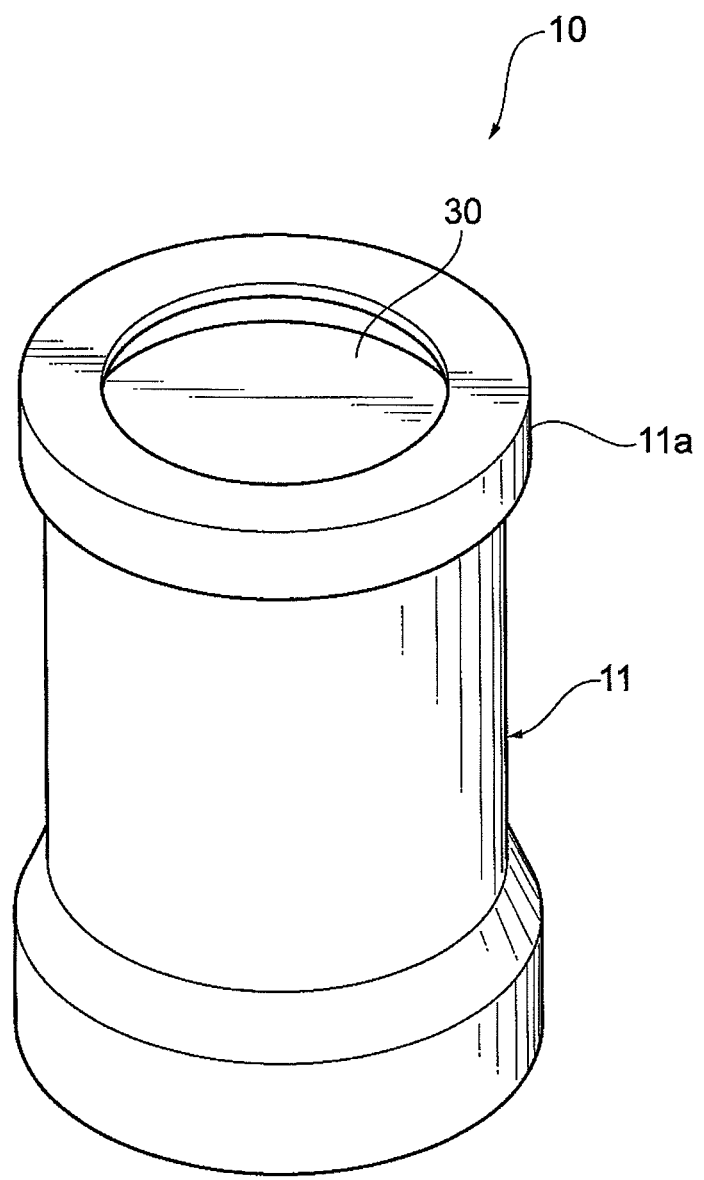
FIG. 1 is a perspective view illustrating an applicator in accordance with an embodiment from the upper part.

Embodiments according to the present invention will now be described in detail with reference to the accompanying drawings. In the explanation of the drawings, same or similar components are denoted by the same reference numerals, and an overlapping explanation thereof will be omitted.

Figure 2:
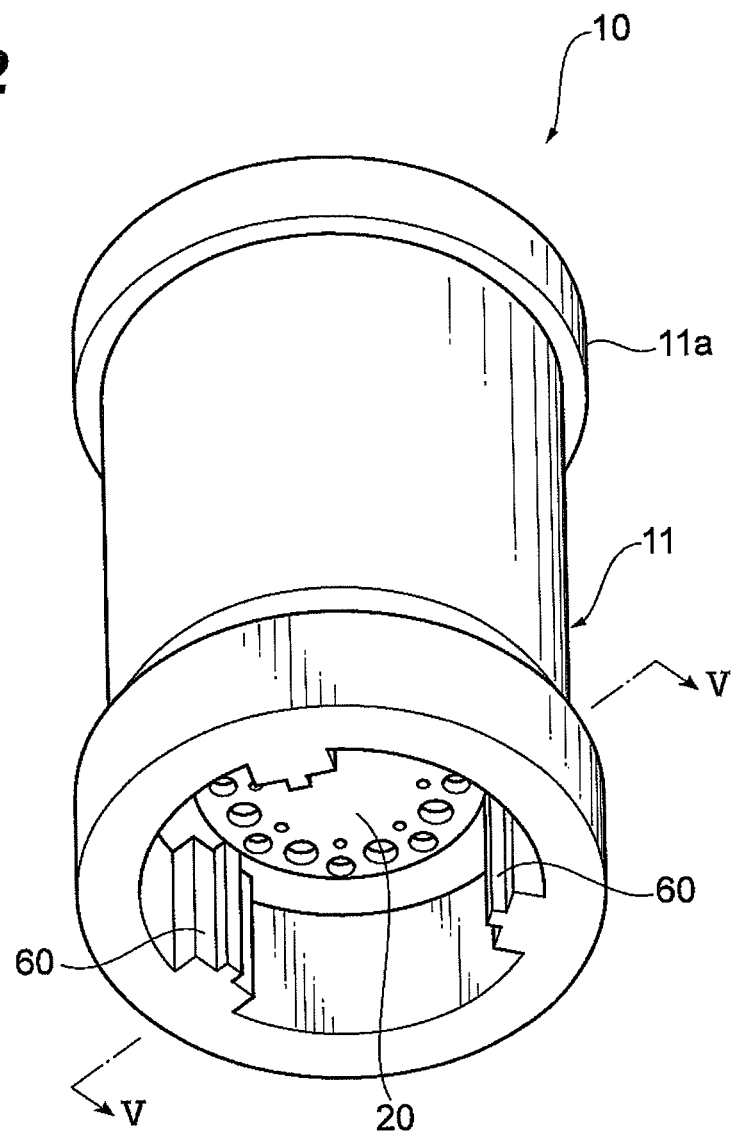
FIG. 2 is a perspective view illustrating the applicator illustrated in FIG. 1 from the lower part.
Figure 3:
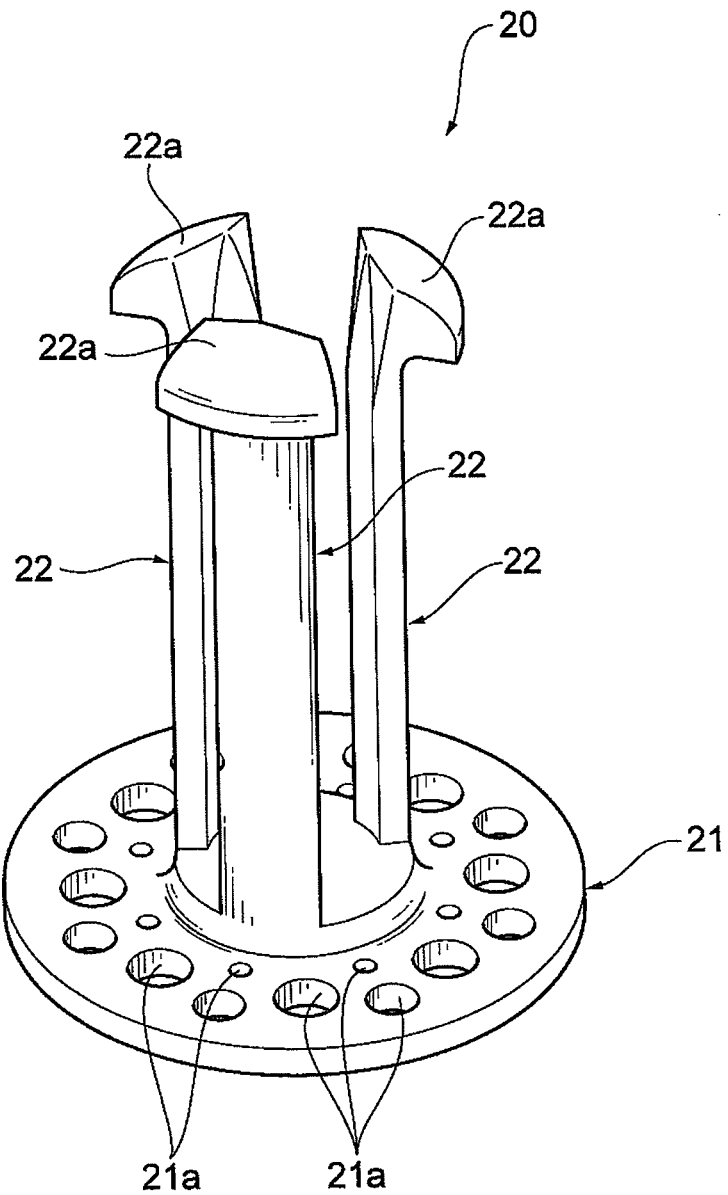
FIG. 3 is a perspective view illustrating a piston illustrated in FIG. 2.
Figure 4:
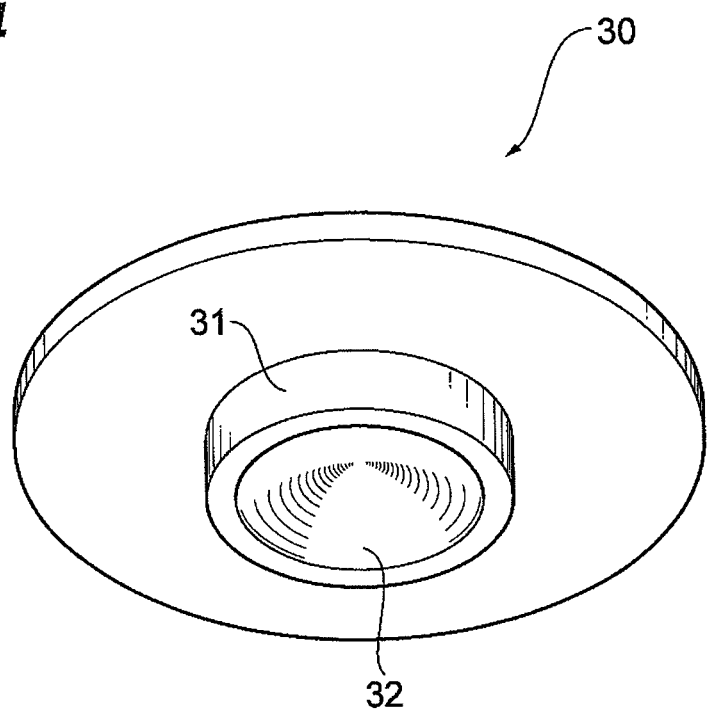
FIG. 4 is a perspective view illustrating a cap illustrated in FIG. 1.

A structure of an applicator 10 in accordance with the embodiment will be described first with reference to FIGS. 1 to 6. FIG. 1 is a perspective view illustrating the applicator 10 from the upper part. FIG. 2 is a perspective view illustrating the applicator 10 from the lower part. FIG. 3 is a perspective view illustrating a piston 20. FIG. 4 is a perspective view illustrating a cap 30. FIG. 5 is a sectional view along line V-V of FIG. 2, and FIG. 6 is a sectional view illustrating a state where claw parts illustrated in FIG. 5 are fixed.

A housing 11 of the applicator 10 has a cylindrical shape. In the applicator 10, the shape of the housing may be changed or a housing surface may be processed in consideration of ease of holding the housing, and easiness of applying micro projections (microneedles) to a skin. For example, a tubular housing having a polygonal cross-section shape may be used, an outer wall may be rounded as a whole, or recesses or steps may be provided to a cylindrical housing. Fine grooves may be formed on or coating may be applied on a surface of the housing in order to prevent slipping.

The piston 20 for making an impact on a microneedle array put on a skin is stored in the vicinity of one end of the housing 11 (see FIG. 2). The cap 30 for activating the piston 20 is stored in the vicinity of the other end of the housing 11 (see FIG. 1). Hereinafter, the side where the cap 30 is stored is defined as the upper side of the applicator 10 or the housing 11, whereas the side where the piston 20 is stored is defined as the lower side of the applicator 10 or the housing 11. An annular member 11*a* is fitted into the upper end of the housing 11, and the lower end of the housing 11 is formed in a tapered shape expanding toward its downside.

The piston 20 is a transmission member that includes a disk-shaped piston plate 21 colliding with the microneedle array, and a plurality of piston rods 22 as illustrated in FIG. 3. The piston rods 22 extend from the vicinity of the center of the upper surface of the piston plate 21 in the direction orthogonal to the upper surface thereof. A plurality of air holes 21*a* for releasing air are provided to the piston plate 21, thereby reducing air resistance and reducing the weight of the piston 20. Hook-shaped claw parts 22*a* projecting outside in a diameter direction of the piston plate 21 each are provided to the tip ends of the respective piston rods 22. The claw parts 22*a* are formed in a tapered shape narrowing toward the tip ends of the piston rods 22.

The shape of the cap 30 is disk-shaped as illustrated in FIG. 4, and its diameter is substantially the same as the inner diameter of the housing 11. A cylindrical projection part 31 is provided on the center of the lower surface of the cap 30, and a recessed part 32 is provided to the projection part 31. A shape of the recessed part 32 is conical so as to receive the claw parts 22*a* of the piston rods 22.

A partition wall 12 for partitioning the inside of the housing 11 into the upper side part and the lower side part is provided in the vicinity of the upper part inside the housing 11 as illustrated in FIG. 5. Hereinafter, a space over the partition wall 12 is referred to as an upper part space 14, whereas a space thereunder is referred to as a lower part space 15. The center of the partition wall 12 has a round through hole 13. An inner cylinder 16 is attached to the through hole 13 in a state of being inserted from under the through hole 13 to the middle thereof. The inner wall of the inner cylinder 16 is formed in a tapered shape expanding toward its downside, and serves for guiding vertical motion of the piston rods 22.

The upper part of the through hole 13 serves for guiding the projection part 31 of the cap 30, and the diameter of the upper part is the same as that of the projection part 31. The upper end of the inner cylinder 16 positioned in the vicinity of the center of the through hole 13 serves for fixing the piston 20, being engaged with the claw parts 22*a* of the piston rods 22. Hereinafter, the upper end of the inner cylinder 16 is referred to as a claw receiving part 17.

The lower part space 15 stores the piston 20, a compression spring (biasing member or elastic member; hereinafter, simply referred to as "spring") 40 providing biasing force to the piston 20, and an annular spring base (support base) 50 supporting the spring 40 from under thereof. A plurality of guides 60 for sliding the spring base 50 within a predetermined range in the vertical direction are provided on the inner wall of the lower part space 15.

Each of the guides 60 extends from the lower end of the housing 11 to the vicinity of the lower end of the inner cylinder 16, and a substantially lower half area of each guide 60 (lower part of the guide 60) is wider than the remaining upper half area (upper part of the guide 60). Notches (not illustrated) for engaging with the upper part of the guides 60 are provided on the outer periphery of the spring base 50. This structure allows the spring base 50 to slide within the upper part of the guides 60 in the vertical direction. The spring 40 is stored in the lower part space 15 so as to surround the inner cylinder 16. The upper end of the spring 40 is attached to the lower surface of the partition wall 12, whereas the lower end thereof is in contact with the upper surface of the spring base 50. In the embodiment, a column coil spring may be used as the spring 40 as illustrated in FIG. 5.

The piston 20 is stored in the lower part space 15 after the spring 40 and the spring base 50 are stored in the lower part space 15. The diameter of the piston plate 21 is substantially the same as the inner diameter of the housing 11 limited by the lower part of the guides 60. The diameter of the piston plate 21 is larger than the inner diameter of the spring base 50, and the piston plate 21 is always positioned lower than the spring base 50.

The piston 20 can be fixed in a state of resisting the biasing force of the spring 40 in the lower part space 15. When the piston plate 21 is pushed from the outside of the housing 11 against the biasing force of the spring 40 in an initial state of the applicator 10 (see FIG. 5), the claw parts 22*a* of the respective piston rods 22 pass through the inner cylinder 16, and are hooked to the claw receiving part 17 as illustrated in FIG. 6. This allows the piston 20 to be fixed in a state of resisting the biasing force of the spring 40.

The cap 30 is stored in the upper part space 14 with the projection part 31 facing the partition wall 12. When the whole cap 30 is stored in this manner, the annular member 11a is attached to an end part thereof. This can prevent the cap 30 from jumping out of the housing 11.

Figure 6:
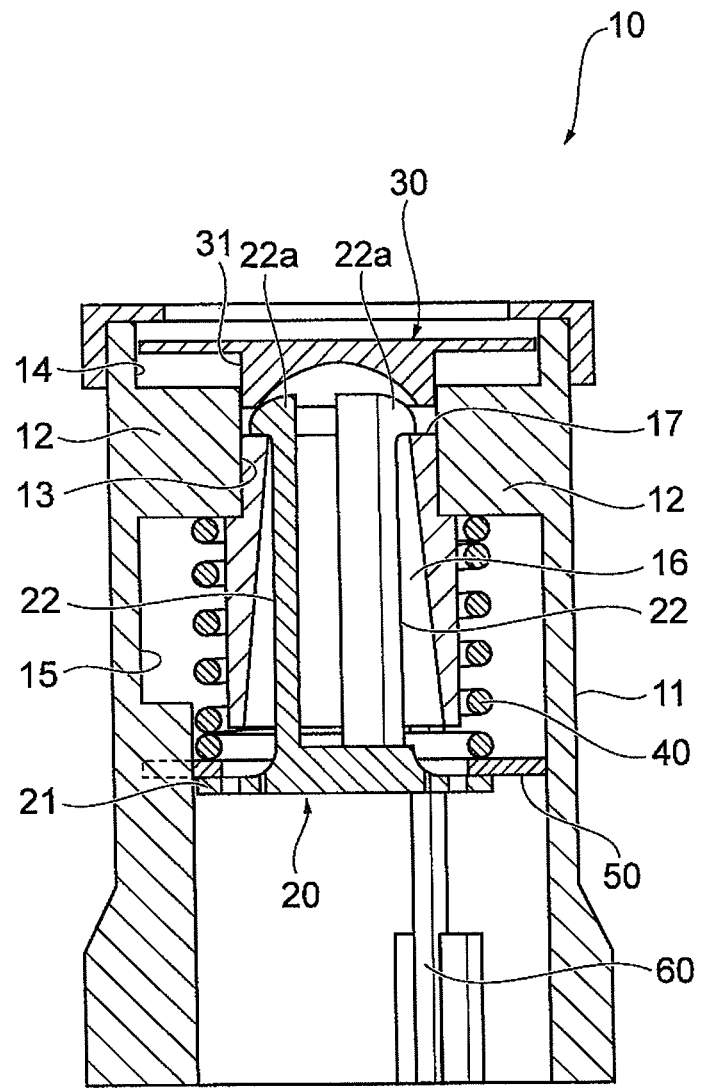
FIG. 6 is a sectional view illustrating a state where claw parts illustrated in FIG. 5 are fixed.

The position of the cap 30 is not fixed in the upper part space 14, and the cap 30 can freely move along an extending direction (vertical direction) of the housing 11 in the upper part space 14. When the applicator 10 is inclined so that the cap 30 is positioned higher than the piston 20, which is fixed in a state of resisting the biasing force of the spring 40, the projection part 31 of the cap 30 is in contact with the claw parts 22a of the piston 20 as illustrated in FIG. 6. In other words, the cap 30 is provided freely movable along the extending direction of the housing 11 in the upper part space 14 so that the projection part 31 can be in contact with the claw parts 22a when the piston 20 is fixed by the claw parts 22a.

Examples of parameters related to energy of the piston 20 activated by the biasing force of the spring 40 include a transverse elasticity modulus, a wire diameter, the number of windings, an average coil diameter, a distance indicating how long the spring 40 is shortened from its natural length, the speed of the piston, the mass of the spring, and the mass of the piston.

The transverse elasticity modulus is determined by a material of the spring, and is 68500 N/mm² when the material is stainless and is 78500 N/mm² when the material is a piano wire (steel). Estimated values of the other parameters are as follows. The wire diameter is from 0.1 to 5 mm, the number of windings is from 1 to 20, the average coil diameter is from 1 to 30 mm, the distance is from 1 to 100 mm, the speed is from 0.1 to 50 m/s, the mass of the spring is from 0.1 to 5 g, and the mass of the piston is from 0.1 to 20 g. In the embodiment, the mass of the piston may be 1.5 g or less.

Theoretical formulae related to the spring and the piston are defined with the parameters below. Equation (1) indicates a relation between the spring constant, the shape of the spring, and the material; Equation (2) indicates a relation between the mass and the size of the spring; Equation (3) indicates a relation between the spring energy and the kinetic energy; and Equation (4) indicates a relation between the speed, the energy, and the mass of the piston. In the following formulae, "G" indicates the transverse elasticity modulus (N/m²); "d" indicates the wire diameter (m); "n" indicates the number of windings; "D" indicates the average coil diameter (m); "k" indicates the spring constant (N/m); "x" indicates the distance (m); "v" indicates the speed (m/s); "l" indicates the length of the spring in its extension (m); "ρ" indicates the density (kg/m³); "m" indicates the mass of the spring (kg); and "M" indicates the mass of the piston (kg). In the description, the kinetic energy is considered to be the same as energy (puncture energy) when the micro projections (microneedles) puncture skin.

[Math. 1]
$$k = \frac{Gd^4}{8nD^3} \quad (1)$$

[Math. 2]
$$m = \frac{\rho \pi l d^2}{4} \quad (2)$$

[Math. 3]
$$E = \frac{1}{2}kx^2 = \frac{1}{2}Mv^2 \quad (3)$$

[Math. 4]
$$v = \sqrt{\frac{2E}{M}} \quad (4)$$

The size of the applicator 10 can be determined depending on the size of the microneedle array below, however, how to determine the size is not limited to as follows.

When a lower side opening part of the housing 11 is shaped to fit the shape of the microneedle array and the minimum inner diameter of the opening part is adjusted to fit the outer diameter of the microneedle array, the size of the applicator 10 can be reduced depending on the size of the microneedle array. If the lower side opening part is formed in this manner, the applicator 10 is not shifted to the diameter direction (width direction) against the microneedle array when positioned on the microneedle array. The applicator 10, thus, enables the piston 20 to be applied to the microneedle array while keeping a positional relation parallel to the microneedle array. This allows puncture to be surely performed (improves the reproducibility of puncture).

A material of the applicator is not limited, but is preferably the one that has strength capable of keeping the biasing force of the spring 40. Examples of the material are as follows. Examples of the material of the housing 11 or the cap 30 can include a synthetic resin material such as acrylonitrile-butadiene-styrene (ABS) resin, polystyrene, polypropylene, and polyacetal (POM), a natural resin material, silicon, silicon dioxide, ceramic, and metal (such as stainless, titanium, nickel, molybdenum, chromium, and cobalt). The piston 20 may be produced using the same material as that of the microneedle array.

Air holes may be provided to the housing 11 and the cap 30 similarly to the piston plate 21. This can reduce air resistance of the cap 30 and reduce the weight of the applicator 10.

Figure 7:
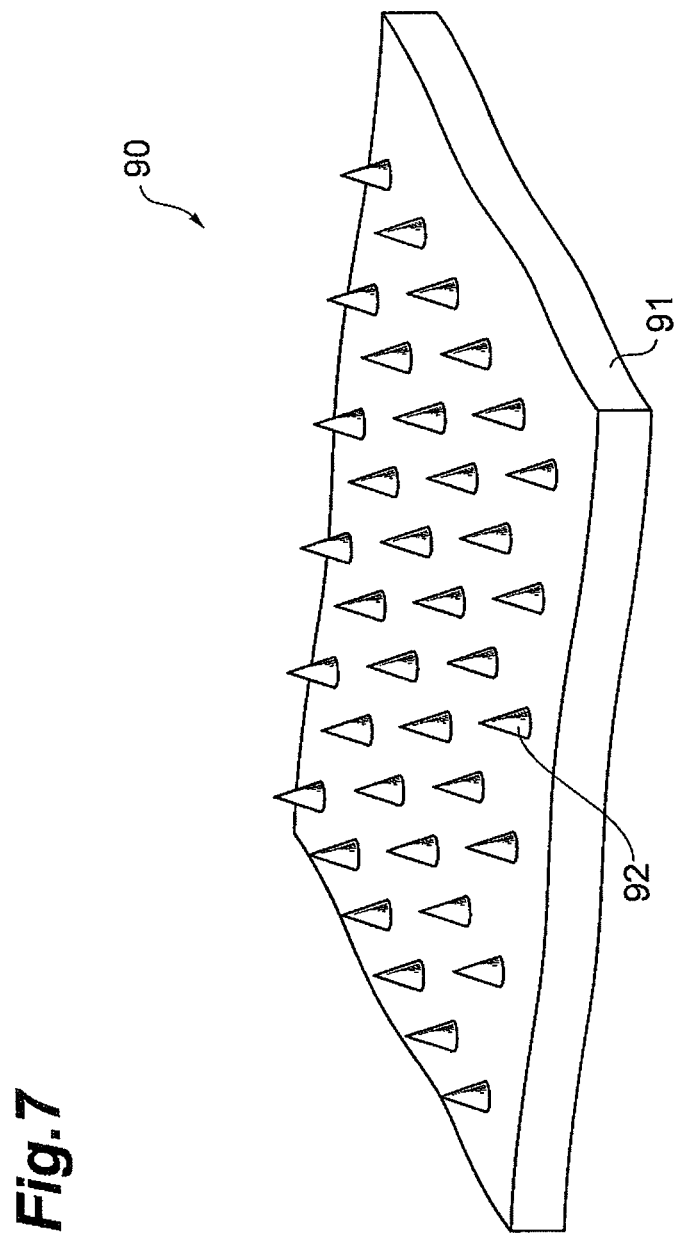
FIG. 7 is a perspective view illustrating a microneedle array.

The following describes the structure of a microneedle array 90 used together with the applicator 10 with reference to FIG. 7. FIG. 7 is a perspective view illustrating the microneedle array 90.

The microneedle array 90 includes a substrate 91 and a plurality of micro projections (needles, in other words, microneedles) 92 two-dimensionally arranged on the substrate 91.

The substrate 91 is a base for supporting the micro projections 92. FIG. 7 illustrates the rectangular substrate 91, but the shape of the substrate 91 is not limited to this and may be round, for example. The micro projections 92 are arranged in zigzag (alternately) at substantially equal intervals on a surface of the substrate 91. A plurality of through holes may be provided to the substrate 91 so as to administer bioactive agents from the back side of the substrate 91 through the through holes. The area of the substrate 91 may be from 0.5 cm² to 10 cm², from 1 cm² to 5 cm², or from 1 cm² to 3 cm². Several substrates 91 may be connected so as to obtain a substrate of a desired size.

Each of the micro projections 92 is a tapered structure narrowing from its bottom part connected to the substrate 91 toward its tip. The tip ends of the respective micro projections may be sharpened or unsharpened. FIG. 7 illustrates the conical micro projections 92, but micro projections having a polygonal pyramid shape such as a square pyramid may be used. The height (length) of the micro projections 92 may be from 20 to 400 μm or from 50 to 300 μm.

One to ten micro projections 92 per 1 mm are provided in one column. An interval between adjacent columns is substantially equal to an interval between adjacent micro projections 92 in one column. The density (needle density) of the micro projections 92, thus, is from 100 to 10000 needles/$cm^2$. The lower limit of the needle density may be 200 needles/$cm^2$, 300 needles/$cm^2$, 400 needles/$cm^2$, or 500 needles/$cm^2$. The upper limit of the needle density may be 5000 needles/$cm^2$, 2000 needles/$cm^2$, or 850 needles/$cm^2$.

Coating of the active agents is applied on the substrate 91 and/or the micro projections 92. The coating is the one in which a coating liquid including the active agent is fixed on a part or the whole of the micro projections 92 and/or the substrate 91. A term "fixed" means to keep a state where an object is approximately uniformly coated with the coating liquid. The coating is applied in a prescribed range including the top of the micro projections 92. This range varies depending on the height of the micro projections 92, and may be from 0 to 500 μm, from 10 to 500 μm, or from 30 to 300 μm. The thickness of the coating may be less than 50 μm, less than 25 μm, or from 1 to 10 μm. The thickness of the coating is an average thickness measured over the surface of the micro projections 92 after drying. The thickness of the coating can be increased by applying a plurality of films of a coating carrier, in other words, by repeating a coating process after the coating carrier is fixed.

Figure 8:
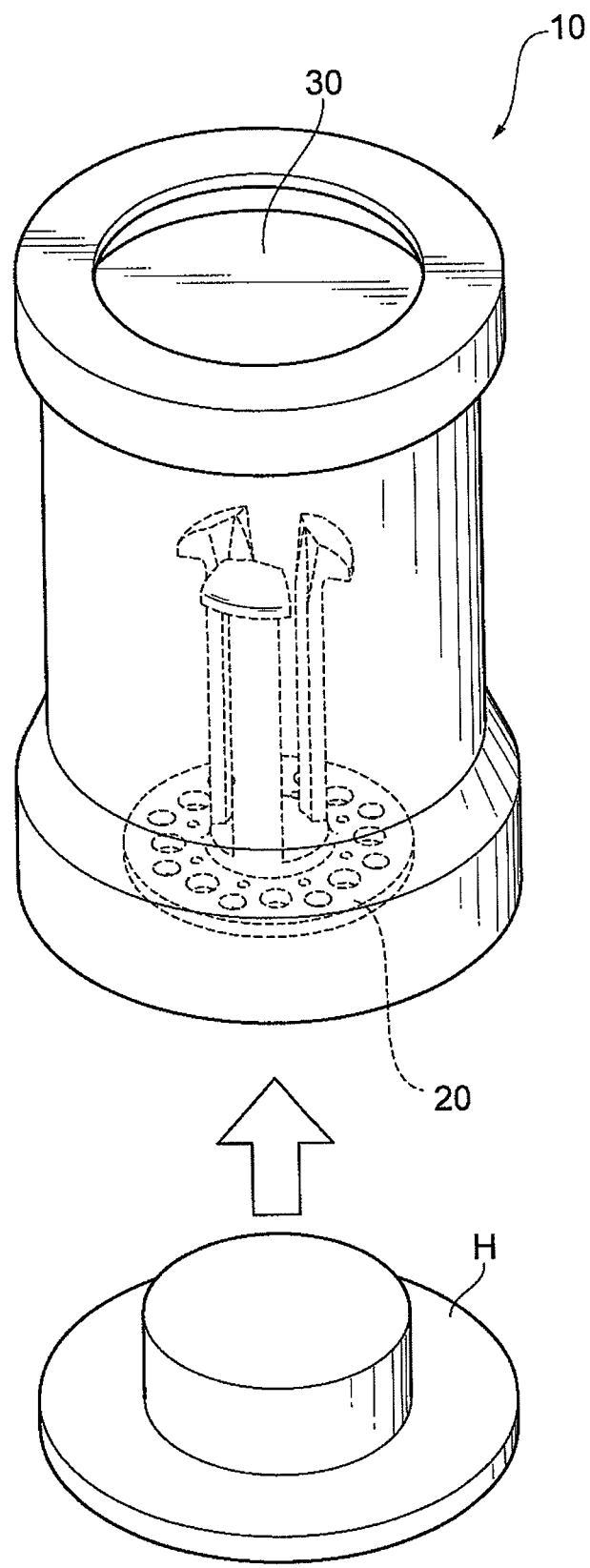
FIG. 8 is a view illustrating a case where an auxiliary tool is employed in use of the applicator illustrated in FIG. 1.
Figure 9:
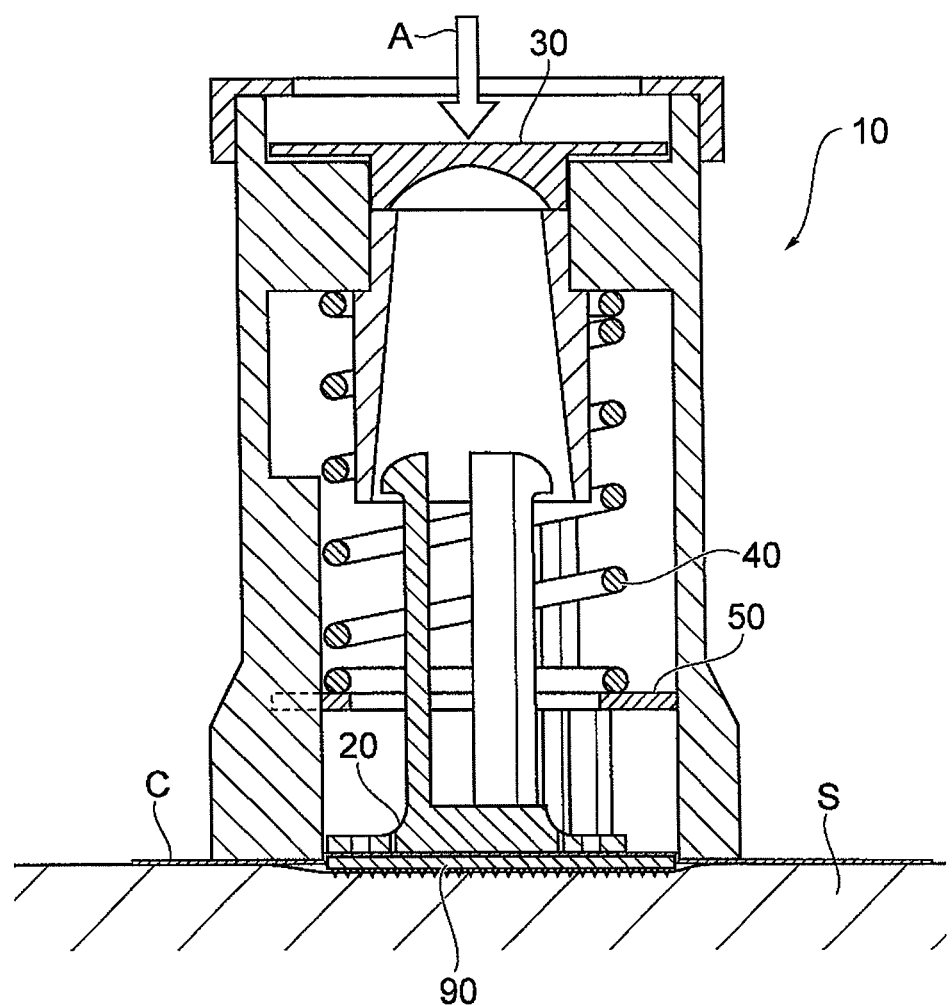
FIG. 9 is a view illustrating how to use the applicator illustrated in FIG. 1.

The following describes how to use the applicator 10 with reference to FIGS. 8 and 9. FIG. 8 is a view illustrating a case where an auxiliary tool H is employed in use of the applicator 10. FIG. 9 is a view illustrating how to use the applicator 10.

Figure 5:
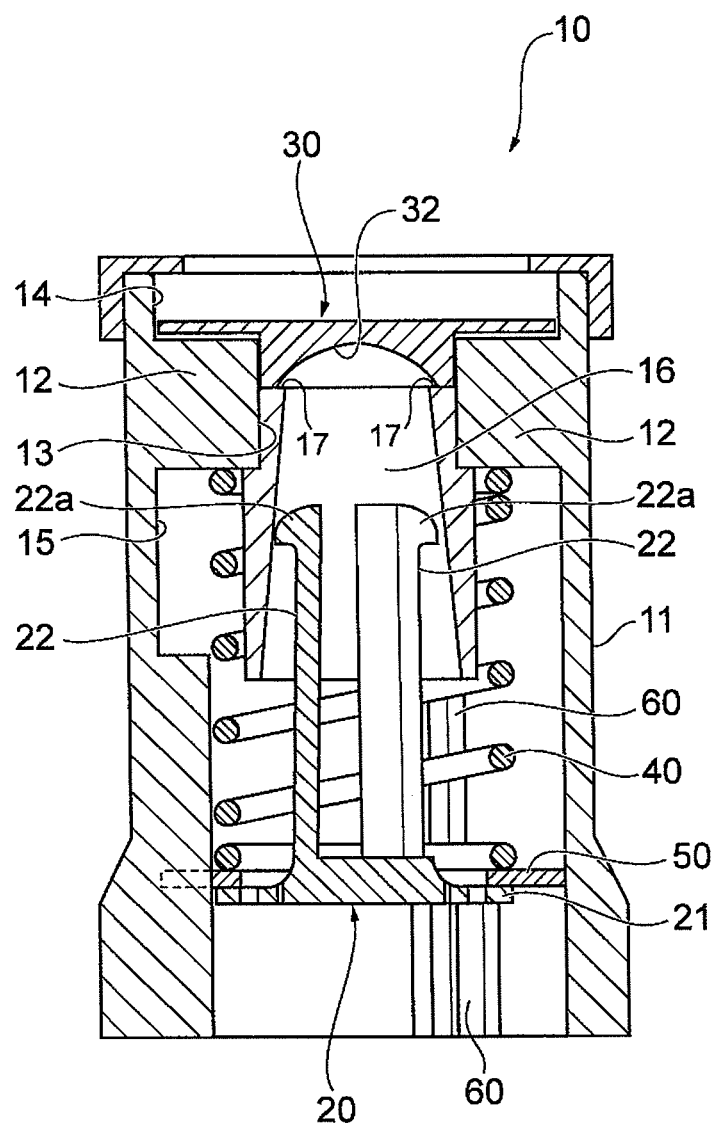
FIG. 5 is a sectional view along line V-V of FIG. 2.

The initial state of the applicator 10 is as illustrated in FIG. 5. The piston 20 in an initial state is pushed inside the applicator 10 by a finger, and the piston 20 is fixed in a state of resisting the biasing force of the spring 40. The piston 20 may be pushed up by a hand or may be pushed up by the auxiliary tool H as illustrated in FIG. 8. The shape of the auxiliary tool H is not limited to an example in FIG. 8. The applicator 10 in which the piston 20 is fixed becomes a state illustrated in FIG. 6. The inner wall of the inner cylinder 16 is formed in a tapered shape narrowing toward the upper end (claw receiving part 17). This allows the user to engage the claw parts 22a with the claw receiving part 17 by a less force and easily fix the piston 20. The user can recognize the completion of fixing with a "clicking" sound. The force to be applied when the piston 20 is fixed can be strengthened or weakened by adjusting an inclination of the tapered shape of the inner cylinder 16.

Subsequently, the applicator 10 is positioned and kept on the microneedle array 90 put on a skin S, and the cap 30 is pushed inside the applicator 10 by a finger (is pushed in an arrow A direction) as illustrated in FIG. 9. The microneedle array 90 may be attached to the skin with a cover agent C before the applicator 10 is positioned as illustrated in FIG. 9.

When the cap 30 is pushed, the projection part 31 provided to its lower surface pushes the claw parts 22a of the respective piston rods 22 toward the center of the through hole 13, so that the engagement between the claw parts 22a and the claw receiving part 17 is released. This causes the fixed state of the piston 20 to be released and allows the piston 20 to move toward the outside of the applicator 10 with the biasing force of the spring 40. The spring base 50 slides within the upper part of the guides 60. Thus, the piston 20 receives the biasing force of the spring 40 (the piston 20 is pushed in the second section by the spring base 50) within a section along the upper part of the guides 60 (second section) through the spring base 50 to move. After the spring base 50 stops at the lower end in the second section, the piston 20 moves in a section along the lower part of the guides 60 (first section) without receiving the biasing force of the spring 40 and collides with the microneedle array 90 at the lower end of the applicator 10 (see FIG. 9).

Thus, it is conceivable that the projection part 31 is a release mechanism for releasing the piston 20 fixed in a state of resisting the biasing force of the spring 40. Since the conical recessed part 32 is provided to the projection part 31, the claw parts 22a is drawn along the conical shape and the piston 20 (applicator 10) is activated only when a certain force is applied to the cap 30. Thus, a constant impact is made if anyone carries out administration. This allows puncture to be surely performed (improves the reproducibility of puncture).

A force necessary for releasing the piston 20 can be adjusted by changing the shape of the recessed part 32 and the shape of the claw parts 22a. For example, if the inclination of the tapered shape of the claw parts 22a is made steep and the inclination of the conical shape of the recessed part 32 is adjusted corresponding thereto, the piston 20 can be released from the fixed state by a small force.

The collision transmits an biasing force of the spring 40 to the microneedle array 90 through the piston 20, whereby the micro projections 92 puncture the skin. The active agents applied on the microneedle array 90 are administered to a body through the micro projections 92.

After the use of the applicator 10 in this manner, the piston 20 can be fixed again in a state of resisting the biasing force of the spring 40 by being pushed inside the applicator 10. The applicator 10, thus, can be used repeatedly.

As described above, in the embodiment, the piston 20 transmitting biasing force necessary for puncture to the microneedle array 90 is very light, and the user feels less impact during operation of the applicator 10. The user, therefore, can administer the active agent using the applicator 10 without fear. In addition, even if the piston 20 is lightened in order not to give fear to the user, the active agent can be effectively administered by properly setting the momentum of the piston 20 and the needle density of the micro projections 92.

EXAMPLE

The present invention will now be specifically described based on embodiments, but is not limited to them at all. The following embodiment shows some examples about the mass and the momentum of the piston and the needle density of the micro projections (microneedles).

Puncture performance was evaluated using the applicator and the microneedle array described in the embodiment. The spring included in the applicator was a column coil spring that was approximately 20 mm in length in an extending state (the height of the spring in an extending state is referred to "free height") and was approximately 10 mm in length in a compressed state. The puncture performance was evaluated by administering ovalbumin (OVA) to a human skin (in vitro) with the microneedle array so as to obtain the transfer amount of OVA to the human skin. The transfer amount means an amount that is administered to the skin out of OVA fixed on the micro projections.

There were prepared four types of pistons each having different mass as follows: 0.9802 g; 1.1906 g; 1.6509 g; and 2.8603 g. There were prepared a plurality of kinds of springs each having different spring constants in order to obtain various momentum P for the respective pistons. Herein, the momentum P (N·s) of the piston is represented by "P=my", where "m" is the mass of the piston (kg) and "v" is the speed of the piston (m/s). The momentum P of the piston is an index for puncture energy when the micro projections (microneedles) collide with the human skin.

There were prepared three types of polylactic acid microneedle arrays (array A, array B, and array C). In each of the microneedle arrays, the height of the micro projection was 500 μm, and the area of the flat part at its tip was from 64 to 144 μm². In each of the microneedle arrays, the coating range was approximately 180 μm including the top of the micro projections when OVA was applied on the respective micro projections. The differences among three types of microneedle arrays are the number of micro projections, the area of the substrate, the needle density, and an initial content (total amount) of OVA. Specific values are as shown in Table 1.

TABLE 1

| | Array A | Array B | Array C |
|---|---|---|---|
| Number of micro projections | 640 | 640 | 1336 |
| Area of substrate (cm²) | 1.13 | 2.26 | 2.26 |
| Needle density (needles/cm²) | 566 | 283 | 591 |
| Initial content (μg) | 51 | 44 | 96 |

After the microneedle array in a state where the micro projections were coated with OVA was left still on the human skin and the applicator was positioned against the microneedle array, OVA was administered to the human skin by activating the applicator to make the piston plate collide with the microneedle array. The microneedle array removed from the human skin after the administration of OVA was soaked in phosphate buffered saline (PBS) so as to extract OVA. The amount of the extracted OVA was subtracted from the initial applied amount so as to obtain the transfer amount and the transfer rate. The speed of the activated piston was measured by a laser displacement gauge called LK-H150, which was made by Keyence corporation. Results shown in FIGS. 10 and 11 were obtained by applying this experiment to various combinations of the piston, the spring, and the microneedle array.

Figure 10:
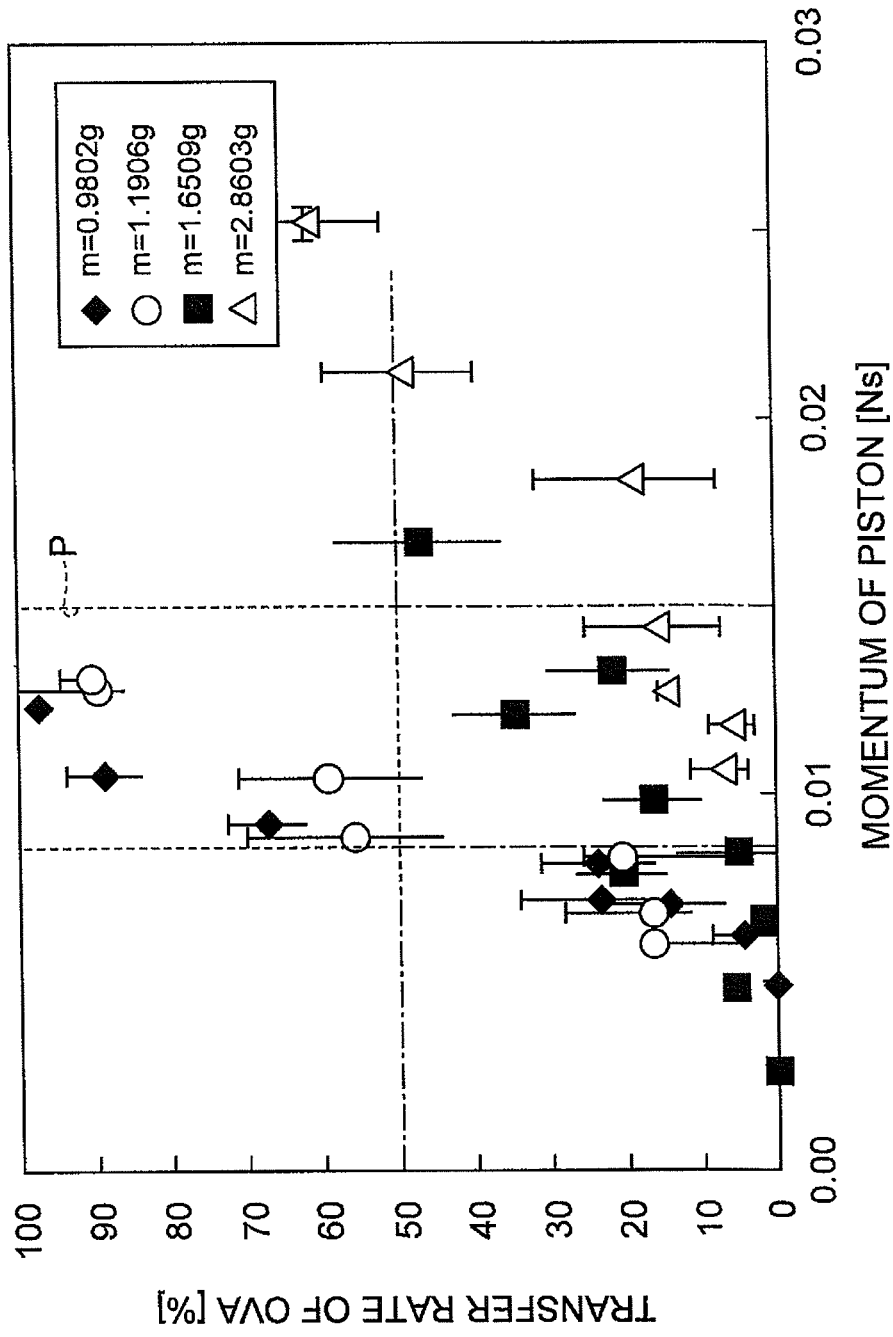
FIG. 10 is a graph illustrating relations between momentums of the pistons and transfer rates of ovalbumin (OVA) in accordance with an example.

A graph in FIG. 10 illustrates transfer rates of OVA in relation with momentums of the pistons. The transfer rate of OVA was obtained by variously changing the combination of the piston and the spring in the microneedle array (i.e., array A) having the substrate area of 1.13 cm² and 640 micro projections. In this graph, an area P surrounded by a dashed line shows the preferred transfer rate. This area P corresponds approximately to a case where the mass of the piston is 1.5 g or less and the momentum of the piston is from 0.0083 (N·s) to 0.015 (N·s).

Figure 11:
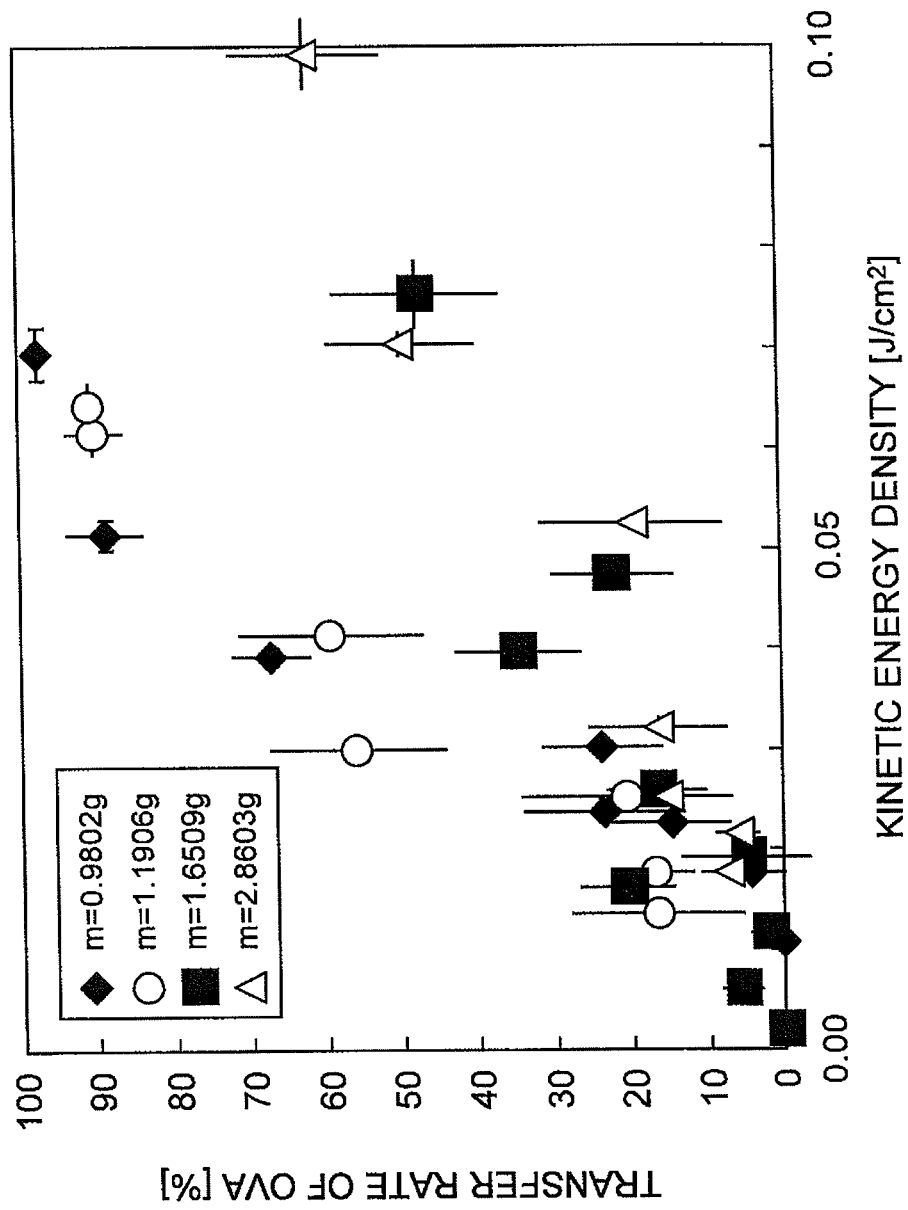
FIG. 11 is a graph illustrating relations between kinetic energy density of the pistons and transfer rates of OVA in accordance with the example.

A graph in FIG. 11 illustrates transfer rates of OVA in relation with kinetic energy density. The transfer rate of OVA was obtained by variously changing the combination of the piston and the spring in the microneedle array having the substrate area of 1.13 cm² and 640 micro projections (i.e., array A). In other words, in the graph in FIG. 11, the abscissa in FIG. 10 is replaced with the kinetic energy density. It was predicted that the transfer rate and the kinetic energy density correspond to each other by one to one (that is, they indicate a proportional relation and have data plotted on the almost same straight line). However, it has been found that, even if the kinetic energy density is the same, the transfer rate may be different depending on the mass and the speed of the piston as illustrated in FIG. 11. Specifically, it has been found that the higher transfer rate can be obtained when a light piston collides with the microneedle array at high speed, compared with a case when a heavy piston collides with the microneedle array at low speed.

Figure 12:
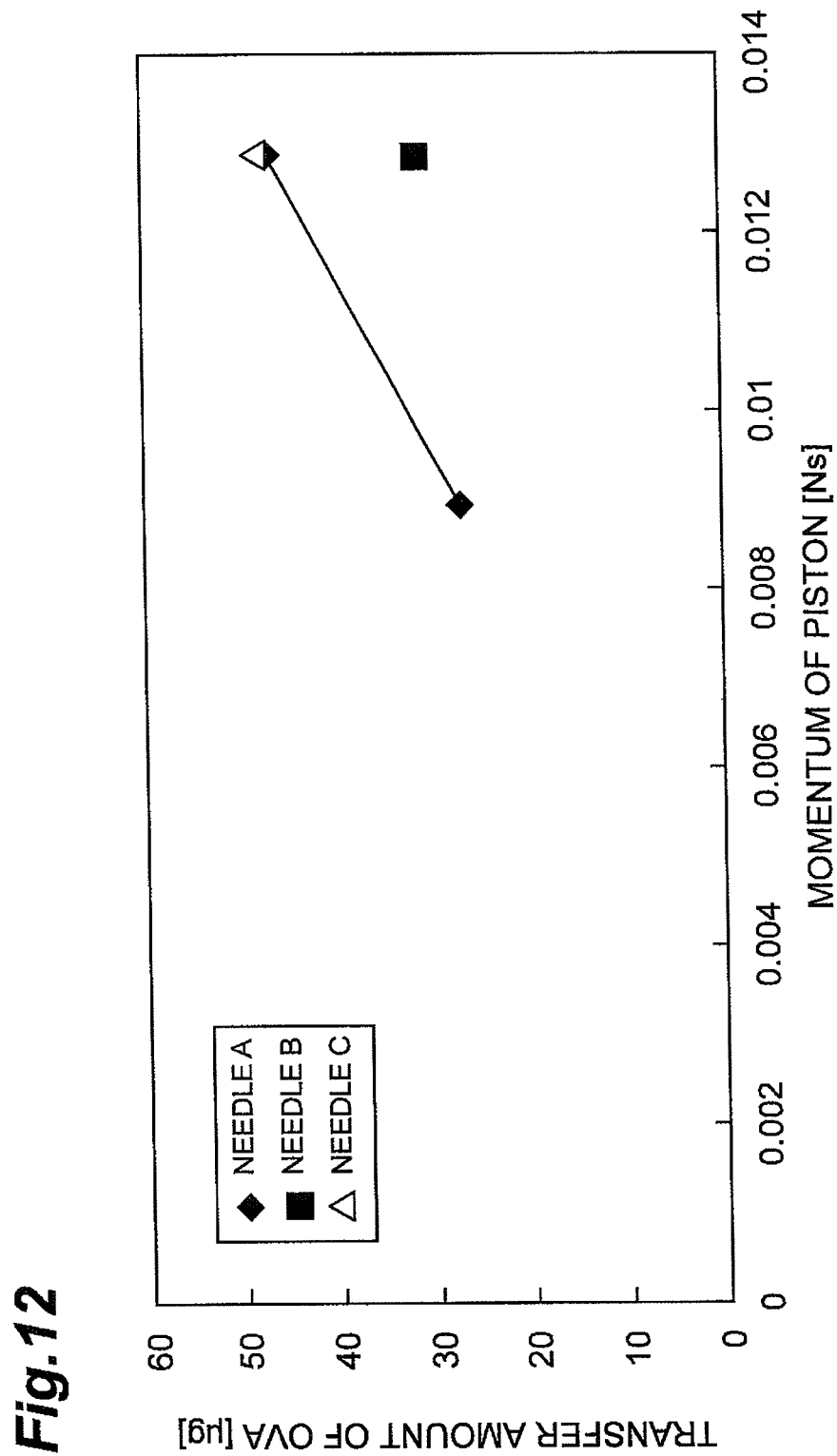
FIG. 12 is another graph illustrating a relation between momentums of the piston and transfer amounts of OVA in accordance with the example.

A graph in FIG. 12 illustrates transfer amounts of OVA obtained by changing microneedle arrays and springs against a piston having a mass of 1.1906 g. This graph shows that the transfer amount is preferable when the needle density was 500 needles/cm² or more (when the array A or array C was used). It has been also found that, when the needle density is 500 needles/cm² or more, the transfer amount is proportional to the momentum of the piston.

The present invention has been described in detail based on the embodiment thereof, but it should be noted that the present invention is not limited to the embodiment. Various changes and modifications can be made without departing from the spirit and scope of the present invention.

Figure 13:
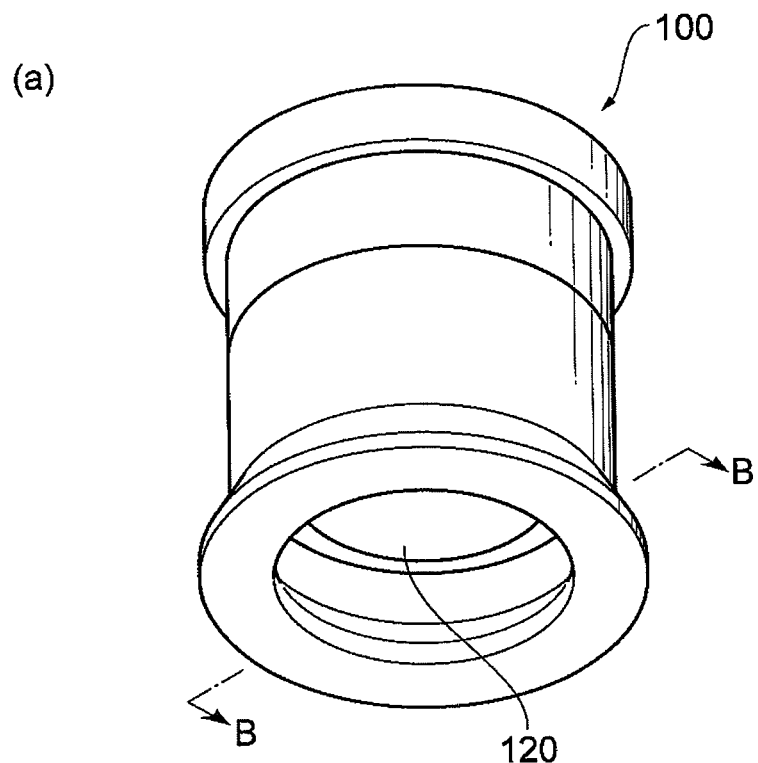
FIG. 13(a) is a perspective view illustrating an applicator in accordance with a modified embodiment.
FIG. 13(b) is a sectional view along line B-B of FIG. 13(a).
Figure 13:
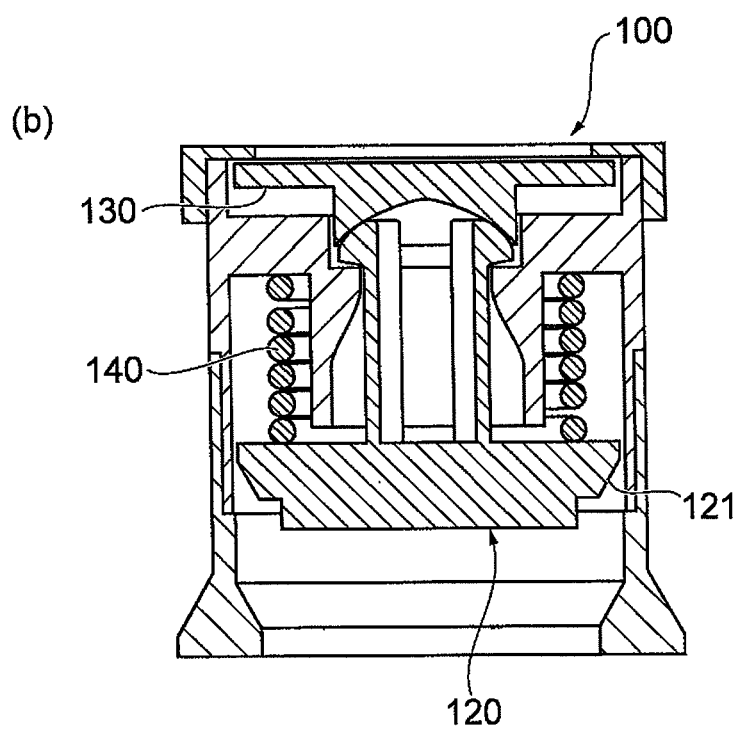

In the embodiment, the piston 20 moves toward the microneedle array without receiving the biasing force of the spring 40 in a part of the movement section, but the piston may keep receiving biasing force in the whole movement section (in other words, all during operation). For example, the present invention can be applied to an applicator 100 in which the lower end of a spring (biasing member) 140 is in contact with the upper surface of a piston plate 121 as illustrated in FIG. 13. In this case, a cap 130 is pushed in the same manner as the case of the applicator 10 so as to activate a piston (transmission member) 120, whereby the piston 120 is continuously pushed by the spring 140 until the piston 120 reaches the lower end of the applicator 100.

Figure 14:
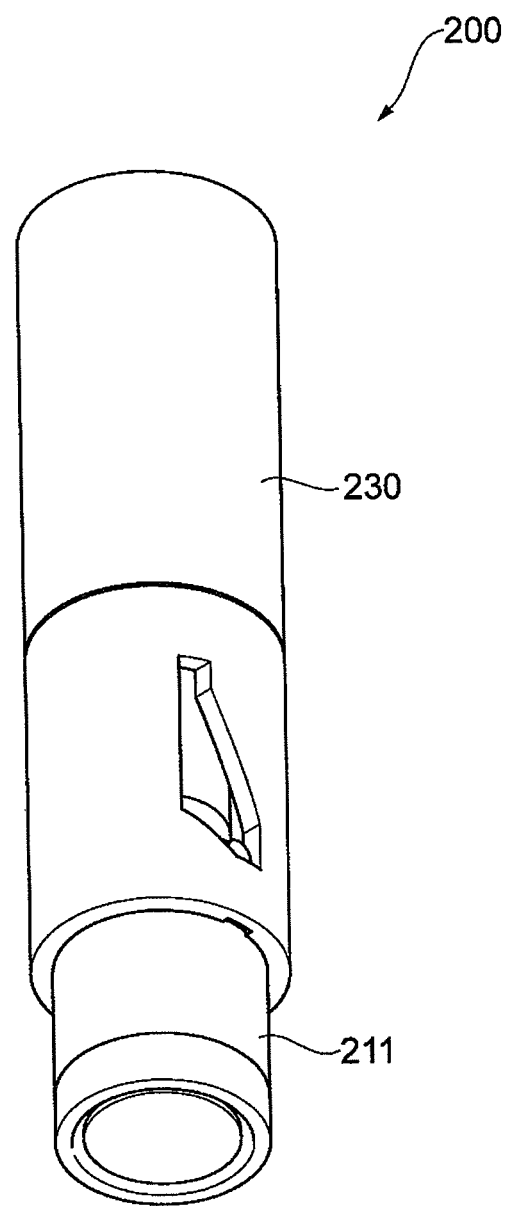
FIG. 14 is a perspective view illustrating an applicator in accordance with another modified embodiment.

The present invention can be applied to an applicator 200 illustrated in FIGS. 14 and 15. The applicator 200 includes a main body 211 and a cap 230. The main body 211 stores a piston 220 transmitting the biasing force of a spring 240 to the microneedle array. The piston 220 includes a rod-like member 222 activated by the spring 240 and a transmission plate (transmission member) 221 provided to the lower end part of the rod-like member 222. The transmission plate 221 is not fixed to but hooked to the rod-like member 222 in a state of imparting a shaft directional play of the rod-like member 222. When the piston 220 is activated by the spring (biasing member) 240, first the rod-like member 222 and the transmission plate 221 integrally move downward. Then, the transmission plate 221 continuously drops to the lower end of the applicator 200 and transmits the biasing force of the spring 240 to the microneedle array, whereas the lower end of the rod-like member 222 stops above the lower end of the applicator 200. For details on the applicator 200, refer to the description of Japanese Patent Application No. 2011-164723 that the applicant filed prior to this application.

The spring is used as the biasing member in the embodiment, but the biasing member is not limited to this. For example, a mechanism in which a jet of compressed gas causes the piston to collide with the microneedle array may be adopted as the biasing member.

The microneedle array 90 and the applicator 10 are independent in the embodiment, but the microneedle array 90 may be integrated with the applicator 10. Specifically, the microneedle array 90 may be integrated with the surface of the piston plate 21 (surface opposite to the piston rods 22). Examples of integrating the microneedle array 90 with the piston plate 21 include a case in which the microneedle array 90 is bonded to the piston plate 21 by an adhesive or other means, a case in which the microneedle array 90 is mechanically fitted to the piston plate 21 by a claw member or other members, and a case in which micro projections (microneedles) are directly formed on the piston plate 21 using integral forming or other methods.

REFERENCE SIGNS LIST

10 . . . applicator, 11 . . . housing, 20 . . . piston, 30 . . . cap, 40 . . . spring, 90 . . . microneedle array, 92 . . . micro projections (microneedles), 100 . . . applicator, 120 . . . piston, 130 . . . cap, 140 . . . spring, 200 . . . applicator, 220 . . . piston, 230 . . . cap, 240 . . . spring.

The invention claimed is:

1. An applicator applying microneedles to a skin, the applicator comprising:
    a transmission member that transmits biasing force of a biasing member to a microneedle array including microneedles with a needle density of 500 needles/cm$^2$ or more, wherein
    a mass of the transmission member is 1.5 g or less,
    the biasing member is an elastic member,
    the transmission member moves without receiving the biasing force of the elastic member in a first section forming a part of a movement section in which the transmission member moves toward the skin,
    a momentum of the transmission member activated by the biasing force of the biasing member is from 0.0083 (N·s) to 0.015 (N·s), wherein
    the applicator further comprises a support base supporting the elastic member and transmits the biasing force to the transmission member in a second section different from the first section, and wherein
    the support base pushing the transmission member with the biasing force stops at one end of the second section, whereby the transmission member moves without receiving the biasing force in the first section.

2. The applicator according to claim 1, wherein a transfer amount of an active agent applied on the microneedles to the skin is proportional to the momentum of the transmission member.

3. The applicator according to claim 1, wherein the biasing member is a column coil spring.

* * * * *